United States Patent [19]

Weyer et al.

[11] Patent Number: 5,434,273
[45] Date of Patent: Jul. 18, 1995

[54] PREPARATION OF N-SUBSTITUTED 2-PYRROLIDONES

[75] Inventors: Hans-Juergen Weyer, Mannheim; Rolf Fischer, Heidelberg, both of Germany

[73] Assignee: BASF Aktiengesellschaft, Ludwigshafen, Germany

[21] Appl. No.: 191,649

[22] Filed: Feb. 4, 1994

[30] Foreign Application Priority Data

Feb. 5, 1993 [DE] Germany ............... 43 03 334.2

[51] Int. Cl.$^6$ ............ C07D 201/08; C07D 201/16
[52] U.S. Cl. ............................. 548/554; 548/552
[58] Field of Search ........................ 548/554, 552

[56] References Cited

U.S. PATENT DOCUMENTS 3,109,005  10/1963  Lidov et al. ............... 260/326.5
3,448,118  6/1969  Chichery ................... 260/326.5
5,157,127  10/1992  Weyer et al. ............... 548/552

FOREIGN PATENT DOCUMENTS 4018243  6/1994  European Pat. Off. .

*Primary Examiner*—David B. Springer
*Attorney, Agent, or Firm*—Keil & Weinkauf

[57] ABSTRACT

The preparation of N-substituted 2-pyrrolidones (I) by the reaction of maleic acid, fumaric acid, or succinic acid or functional derivatives of these acids (compounds II) with a primary amine (III) or by the reaction of amides or imides derived from II and III under hydrogenating conditions in a synthesis stage followed by isolation, by distillation, of I and other volatile components from the resulting reaction mixture, in which the residues present following distillation are subjected to further hydrogenation treatment and the compound (I) thus formed is isolated by distillation.

4 Claims, No Drawings

PREPARATION OF N-SUBSTITUTED 2-PYRROLIDONES

The present invention relates to an improved process for the preparation of N-substituted 2-pyrrolidones (I) by the reaction of maleic acid, fumaric acid, or succinic acid or functional derivatives of these acids (compounds II) with a primary amine (III) or by the reaction of amides or imides derived from II and III under hydrogenating conditions in a synthesis stage followed by isolation, by distillation, of I and other volatile components from the resulting reaction mixture.

The prior art includes the preparation of N-substituted 2-pyrrolidones from a large number of compounds by catalytic hydrogenation. The starting compounds concerned are mixtures of a primary amine (II) and maleic anhydride (DE-A 4,018,243, U.S. Pat. No. 3,109,005) or fumaric acid, maleic acid, succinic acid, functional derivatives of these acids such as succinic anhydride, or amides and imides derived from II and the acids mentioned, all of which can be hydrogenated to produce N-substituted 2-pyrrolidones. Irrespective of the nature of these starting materials the reaction mixtures obtained after hydrogenation are worked up by distillation. On account of their volatility, the desired pyrrolidones, the more volatile pyrrolidines and the less volatile succinic imides can be separated by distillation. Under the distillation conditions, open-chained succinic amides undergo ring closure to form cyclic imides and may thus also be separated. Following distillation, high-boiling residues remain. These residues, which have hitherto been destroyed by burning, are usually equal to a few percent molar of the starting compounds; but under hydrogenation conditions, which produce the corresponding pyrrolidones with particularly high selectivity, this quantity of residuum can be considerably larger.

It is thus an object of the present invention to provide a process by means of which desired products can be isolated from said high-boiling distillation residues.

Accordingly, we have found the process defined above, wherein the residues present following distillation are subjected to further hydrogenation treatment and the compound (I) thus formed is isolated by distillation.

The high-boiling distillation residues involved in the process of the invention are usually products which are not volatile at temperatures below 200° C. under a pressure of ca 10 mbar. These products are presumed to be oligomeric, possibly substituted, succinic diamides. These distillation residues are subjected to renewed hydrogenation.

The hydrogenation is carried out over conventional hydrogenation catalysts, and the catalytically active component contains a Group 8–10 metal, as listed in the Periodic Table, chromium, manganese, rhenium, or copper.

The catalysts used in the process of the invention can be either supported catalysts or solid catalysts ie, unsupported catalysts. Conventional support materials can be used such as activated charcoal, silicon dioxide, aluminum oxides, titanium dioxides, zirconium oxide, silicates, or zeolites.

The catalysts are preferably activated with hydrogen prior to their use in the process of the invention. The active catalyst components present after calcination, generally in the form of their oxides, are reduced to a major extent, usually to the corresponding metals.

The catalysts can be used in the form of suspension catalysts or fixed-bed catalysts. The reaction can be carried out in stirred autoclaves or tubular reactors. If tubular reactors are used, the starting materials can be passed over the catalyst in a packed bubble column or a trickle bed column. The reaction can be carried out continuously or batchwise.

The hydrogen can be fed to the reaction in stoichiometric amounts but preferably in superstoichiometric amounts. The amount of excess hydrogen added is not crucial, since this can be recycled to the reaction. The hydrogenation reaction is generally carried out at temperatures ranging from 100° to 350° C. and preferably from 150° to 300° C. and in particular at from 160° to 280° C., and it is usual to operate at pressures of from 50 to 350 bar and preferably from 100 to 300 bar.

The hydrogenation of distillation residues as proposed in the invention is generally carried out in the presence of a solvent. The solvent used can be virtually any solvent which is inert under the conditions of the hydrogenation, for example, water, aliphatic and aromatic hydrocarbons as well as ethers such as diethyl ether, diisopropyl ether, methyl-tert-butyl ether, dioxane, tetrahydrofuran, or mixtures of these solvents. It is advantageous to use, as solvents, N-substituted 2-pyrrolidones such as are produced in the reaction of the invention. Water is particularly preferred, especially for the preparation of N-methylpyrrolidone. Another possibility is to meter the distillation residues to the hydrogenation reactor in the form of a melt.

The process is not subject to any discernible restrictions as regards the substituents on the nitrogen atom of the N-substituted 2-pyrrolidone. The starting mixtures can contain, as primary amines III, for example, aliphatic amines having from 1 to 10 and preferably from 1 to 4 carbon atoms, primary cycloaliphatic amines having from 5 to 8 carbon atoms, or alternatively primary aromatic and araliphatic amines such as aniline or benzylamine. Bearing in mind the significance of the end products, the amines propylamine, butylamine, hexylamine, decylamine, cyclopentylamine, and cyclohexylamine are of prime importance, as is, in particular, methylamine.

The hydrogenation can take place in the absence of, but preferably in the presence of, the amine used during the formation of the distillation residues. In a preferred embodiment of the process of the invention for the hydrogenation of the distillation residues, these are recycled to the synthesis stage.

Another embodiment of the present invention consists in thermolyzing the high-boiling distillation residues by first subjecting them to a higher temperature than the distillation temperature and then hydrogenating the volatile products thus obtained as described above. Thermolysis also makes it possible to isolate the N-substituted succinic imides formed as the main products and to recycle them to the synthesis stage. The thermolysis of the distillation residues is particularly recommendable when there occurs accumulation of undesirable by-products during feedback of the distillation residues to the hydrogenation stage.

The thermolysis is generally carried out at temperatures ranging from 200° to 500° C. and preferably at from 250° to 400° C. and more preferably at from 280° to 350° C., and it is usual to operate at pressures below 1 bar and preferably at from 0.01 to 100 mbar and in particular at from 1 to 50 mbar.

The product streams obtained by the hydrogenation of distillation residues as proposed in the present invention, exhibit a comparable composition to that of the product achieved by hydrogenating the starting compounds.

The present invention allows for the conversion of high-boiling distillation residues to N-substituted pyrrolidones in good yields. The N-substituted pyrrolidones and especially N-methylpyrrolidone, are mainly used as solvents and extracting agents.

EXAMPLES

Distillation Residues

The high-boiling distillation residues used in the following examples were obtained in the following manner:

An aqueous solution of maleic anhydride and methylamine (20 wt % of maleic anhydride/methylamine, molar ratio 1:1.5) was hydrogenated over a cobalt catalyst at 250° C. and 250 bar. Following subsequent purification, by distillation, of the hydrogenation product stream there were obtained 71% of N-methylpyrrolidone, 5% of N-methylpyrrolidine, and 6% of succinic acid-N-methylimide. There remained 17% of residue (calculated as succinic acid-N-methylamide).

The cobalt catalyst used (prepared by the methods described in DE-A 2,321,101 and DE-A 3,904,083) had the following composition:

63.4 wt % of cobalt, calculated as CoO,
18.1 wt % of copper, calculated as CuO,
6.8 wt % of manganese, calculated as $Mn_3O_4$,
3.1 wt % of molybdenum, calculated as $MoO_3$,
0.15 wt % of sodium, calculated as $Na_2O$, and
3.3 wt % of phosphoric acid.

The hydrogenation catalysts used in the examples were activated with hydrogen in the usual manner, prior to use.

Example 1

The hydrogenation reaction was carried out in a tubular reactor, in which 38 g of the cobalt catalyst were present in a fixed bed. The catalyst was used in the form of 2.5–4 mm gravel.

Using the trickle bed method, there were fed to the reactor at an overall pressure of 200 bar and a temperature of 250° C., 0.15 kg of distillation residues per kilogram of catalyst per hour and 0.55 kg of water per kilogram of catalyst per hour, as well as 2500 L (STP) of hydrogen per kilogram of catalyst per hour.

The yield of N-methylpyrrolidone was 81%, 6% of N-methylpyrrolidine and 7% of succinic acid-N-methylimide also being found. The yields are based on the distillation residues, calculated as succinic acid-mono-N-methylamide.

Example 2

The hydrogenation was carried out in a manner similar to that described in Example 1. The catalyst used comprised 36 g of a nickel catalyst having the following composition: 50 wt % of NiO, 17 wt % of CuO, 31 wt % of $ZrO_2$, and 2 wt % of $MoO_3$ (prepared as described in U.S. Pat. No. 5,037,793) in the form of 4 mm extrudates. Operating under an overall pressure of 200 bar at a temperature of 250° C., there were fed to the reactor 0.2 kg of distillation residues per kilogram of catalyst per hour, 0.1 kg of methylamine per kilogram of catalyst per hour, and 0.7 kg of water per kilogram of catalyst per hour as well as 2500 L (STP) of hydrogen per kilogram of catalyst per hour.

The yield of N-methylpyrrolidone was 67% (based on the distillation residues, calculated as succinic acid-mono-N-methylamide)

Example 3

Thermolysis 50 g of distillation residues were thermolyzed at a pressure of 1 mbar and at a temperature of 280° C. over a period of one hour. The resulting volatile products were removed by distillation and condensed. There remained as bottoms 9.5 g of residue. 24.5 g of succinic acid-N-methylimide were isolated (yield 57% based on the distillation residues, calculated as succinic acid-mono-N-methylamide), which were fed to the synthesis stage.

We claim:

1. In a process for the preparation of N-substituted 2-pyrrolidones (I) by the reaction of maleic acid, fumaric acid or succinic acid or functional derivatives of these acids (compounds II) with a primary amine (III) or by the reaction of amides or imides derived from II and III under hydrogenating conditions in a synthesis stage followed by isolation, by distillation, of I and other volatile components from the resulting reaction mixture, the improvement which comprises passing the residues present following said distillation to the synthesis stage where they are subjected to further hydrogenation and the pyrrolidone compounds (I) thus formed are isolated by distillation.

2. A process as claimed in claim 1, wherein the distillation residues are continuously recycled to the synthesis stage.

3. A process as claimed in claim 1, wherein the distillation residues are first subjected to a higher temperature than that used in the distillation and are then subjected to further hydrogenation treatment.

4. A process as claimed in claim 3, wherein the volatile substances formed during the thermal treatment are removed by distillation and recycled to the synthesis stage.

* * * * *